United States Patent
Hocker et al.

(10) Patent No.: US 10,591,361 B2
(45) Date of Patent: Mar. 17, 2020

(54) EARLY WARNING SYSTEM FOR CONDENSATION INDUCED HYDRAULIC SHOCK

(71) Applicant: Endress + Hauser Flowtec AG, Reinach (CH)

(72) Inventors: Rainer Hocker, Waldshut (DE); Oliver Popp, Oberwil (CH)

(73) Assignee: ENDRESS + HAUSER FLOWTEC AG, Reinach (CH)

(*) Notice: Subject to any disclaimer, the term of this patent is extended or adjusted under 35 U.S.C. 154(b) by 429 days.

(21) Appl. No.: 15/501,003

(22) PCT Filed: Jul. 16, 2015

(86) PCT No.: PCT/EP2015/066259
§ 371 (c)(1),
(2) Date: Feb. 1, 2017

(87) PCT Pub. No.: WO2016/020164
PCT Pub. Date: Feb. 11, 2016

(65) Prior Publication Data
US 2017/0219438 A1   Aug. 3, 2017

(30) Foreign Application Priority Data
Aug. 7, 2014 (DE) .................. 10 2014 111 263

(51) Int. Cl.
*G01K 3/14* (2006.01)
*G01K 13/02* (2006.01)
(Continued)

(52) U.S. Cl.
CPC .............. *G01K 3/14* (2013.01); *G01K 1/024* (2013.01); *G01K 13/02* (2013.01); *G01N 25/08* (2013.01)

(58) Field of Classification Search
CPC .......... G01K 3/14; G01K 1/024; G01K 13/02; G01K 11/02; G01N 25/08
See application file for complete search history.

(56) References Cited

U.S. PATENT DOCUMENTS

| 6,279,593 B1 | 8/2001 | Sheppard | |
|---|---|---|---|
| 2003/0016730 A1* | 1/2003 | Daily | G01K 1/026 374/179 |

(Continued)

FOREIGN PATENT DOCUMENTS

| DE | 945027 C | 6/1956 |
|---|---|---|
| DE | 2946848 A1 | 6/1980 |

(Continued)

OTHER PUBLICATIONS

Barna I. F., Varga L. and Ezsol GY; Steam Condensation Induced Water Hammer Simulations for Different Pipelines in Nuclear Reactor; The 8th International Topical Meeting on Nuclear Thermal-Hydraulics, Operation and Safety (NUTHOS-8); Shanghai, China—Oct. 10-14, 2010; pp. 1-12.

(Continued)

*Primary Examiner* — Natalie Huls
*Assistant Examiner* — Janice M Soto
(74) *Attorney, Agent, or Firm* — Bacon & Thomas, PLLC

(57) ABSTRACT

An apparatus for early warning against condensation induced hydraulic shock in a pipe, conveying a fluid present at least in a first part in the vapor phase and, in the case of condensate formation, in a second part in the form of a condensate, comprising at least two temperature sensors, which are arranged in the pipe and, thus, are fluid contacting, and at least one electronics unit, wherein the first temperature sensor is so arranged that it measures the temperature of the vapor, wherein the second temperature sensor is so arranged that it measures the temperature of the condensate, wherein the at least one electronics unit is so embodied that it ascertains the temperature difference between the temperature of the vapor and the temperature of the condensate, and, upon reaching a predetermined limit value for the temperature difference, generates a report.

10 Claims, 2 Drawing Sheets

(51) Int. Cl.
    *G01K 1/02*     (2006.01)
    *G01N 25/08*     (2006.01)

(56) References Cited

U.S. PATENT DOCUMENTS

| | | | |
|---|---|---|---|
| 2003/0155669 A1* | 8/2003 | Bronshtein | F26B 5/02 264/4.1 |
| 2007/0223303 A1* | 9/2007 | Tessien | B01J 19/008 366/144 |
| 2011/0154912 A1* | 6/2011 | Kumar | G01F 1/8413 73/861.19 |
| 2014/0166115 A1 | 6/2014 | Yang | |

FOREIGN PATENT DOCUMENTS

| | | |
|---|---|---|
| DE | 3113697 A1 | 12/1982 |
| DE | 2414671 C2 | 12/1983 |
| DE | 4300513 A1 | 7/1994 |
| DE | 19624490 A1 | 1/1997 |
| DE | 102004050378 * | 4/2006 |
| DE | 102004050378 A1 | 4/2006 |
| DE | 102014111263 A1 | 3/2016 |
| JP | 2002071092 A | 3/2002 |
| WO | WO03033958 A1 | 4/2003 |

OTHER PUBLICATIONS

German Search Report, German Patent Office, Munich, DE,—dated Jan. 12, 2015.
International Search Report, EPO, The Netherlands,—dated Sep. 29, 2015.
English Translation of the International Preliminary Report on Patentability, WIPO, Geneva, CH,—dated Feb. 16, 2017.

\* cited by examiner

EARLY WARNING SYSTEM FOR CONDENSATION INDUCED HYDRAULIC SHOCK

TECHNICAL FIELD

The invention relates to an apparatus and to a method for early warning against condensation induced hydraulic shock in a component conveying a fluid. In such case, the fluid is present at least in a first part in the vapor phase and in the case of condensate formation in a second part in the form of a condensate.

BACKGROUND DISCUSSION

The terminology, hydraulic shock, covers a number of physical phenomena, in the case of which water produces a strong mechanical shock. The cause rests in the small compressibility of water. In the case of systems of vapor in the form of steam, hydraulic shocks occur in the form of condensation shocks, which are observable, among others, in the case of pressure increases. In principle, three phenomena are distinguished in this regard, which all fall under the label, condensation induced hydraulic shock. One speaks of steam hammer, when steam bubbles implode in water. Occasionally, this principle is referred to in the literature also as hydraulic shock. A droplet impact, in contrast, is present, when droplets impact with high velocity on a surface. And, finally, cavitation refers to a microscopic form of steam hammer.

Condensation induced hydraulic shocks are of importance in vapor systems, pipes containing a condensing gas, especially vapor lines, however, also boilers or thermal solar plants. For example, they can occur in the case of heating a fluid by targeted introduction of vapor into a liquid. However, also during operation, unwanted condensation induced hydraulic shock can occur, when condensate is insufficiently removed from the respective media-containing component such as a container, boiler or pipe, and hot vapor flows into the cold liquid. As a result, pressure spikes of up to a number of hundred bar can arise with the possible result of severe damage to the respective component. Condensation induced hydraulic shock belongs to the most frequent causes of significant accidents, for example, in steam power plants or steam boiler plants.

The underlying mechanisms are known from a large number of publications. In the following, by way of example, the occurrence of steam hammers will be described in greater detail. When a steam bubble is entrained within a very much colder condensate, the steam bubble is cut off, e.g insulated, from further steam-, respectively energy, supply. As a result, the steam bubble transfers its energy to the condensate and cools down to the temperature of the condensate. Correspondingly, also the pressure in the steam bubble falls from a starting value of some bar to a few mbar. Due to the high heat transfer coefficient between steam and condensate, this chain of events occurs in a very short time interval, usually within a few milliseconds.

During this chain of events, the condensate surface, which surrounds the steam bubble, collapses toward the center of the steam bubble. In the center, the surfaces of the condensate coming from the different spatial directions impact on one another. Correspondingly, high pressure spikes occur, which lead spontaneously, however, also as a result of repeated occurrences, to significant damage to the respective media-containing component as well as to measuring apparatuses possibly mounted therein, respectively thereto, until a bursting occurs with resultant escape of the respective medium into the environment.

The conditions for the occurrence of steam hammers in a pipe flowed through by a fluid are listed, for example, in the Proceedings of the 8th International Topical Meeting on Nuclear Thermal-Hydraulics, Operation and Safety in the paper by I. F. Barns, L. Varga and Gy. Ézsöl entitled "Steam Condensation Induced Water Hammer Simulation for Different Pipelines in Nuclear Reactor" (http://www.kfki.hu/~barnai/N8P0220.pdf, downloaded on Aug. 1, 2014):

a) The pipeline must be horizontal.
b) The temperature difference between steam and condensate must be at least 20K.
c) The ratio of length to diameter of the pipeline must be greater than 24.
d) The Froude number, which is the ratio of inertial forces to gravitational forces within a hydrodynamic system, must be less than 1.
e) The neighboring steam volume must be sufficiently large.
f) The occurring pressure spikes must be at least 10 bar over the maximum allowable operating pressure, in order to bring about significant damage.

The list makes clear that the occurrence of condensation induced hydraulic shock, especially water hammer, depends, as a rule, on a number of factors acting together. The prediction of when a condensation induced hydraulic shock, especially a steam hammer, will occur is, correspondingly, in no way trivial. Since, however, the damage caused thereby can be immense, an early warning system for the occurrence of condensation induced hydraulic shock would be desirable.

SUMMARY OF THE INVENTION

An object of the present invention is therefore to provide an apparatus, which, reliably and early, detects the possible occurrence of condensation induced hydraulic shock.

This object is achieved according to the invention by an apparatus for early warning against condensation induced hydraulic shock in a component, especially a pipe, conveying a fluid present at least in a first part in the vapor phase and, in the case of condensate formation, in a second part in the form of a condensate, comprising at least two temperature sensors, which are arranged in the pipe and, thus, are fluid contacting, and at least one electronics unit, wherein the first temperature sensor is so arranged that it measures the temperature ($T_V$) of the vapor, wherein the second temperature sensor is so arranged that it measures the temperature ($T_K$) of the condensate, wherein the at least one electronics unit is so embodied that it ascertains the temperature difference between the temperature of the vapor and the temperature of the condensate, and, upon reaching a predetermined limit value for the temperature difference, generates a report. The temperature difference is thus a measure for the probability of occurrence of condensation induced hydraulic shock. After reaching a temperature difference, which corresponds to the predetermined limit value, there is, correspondingly, a significant probability, so that a report is generated.

Of course, the invention also includes other types of media conveying components, such as described above.

The principle of evaluating the temperature difference between vapor and condensate is based on the following analysis of the above mentioned conditions for the occurrence of condensation induced hydraulic shock in a pipe:

The conditions a), c) and e) are normally fulfilled in a typical vapor system, respectively vapor distribution system, since the respective pipes or pipelines are arranged unavoidably essentially horizontally over extended distances. In this way, implicitly, also the vapor volume is quite large.

The condensate is located, as a rule, in the lower region of the pipeline. Because of the typically low gradient in pipelines arranged essentially horizontally, the flow velocity of the condensate is very small. Therefore, also condition d) is fulfilled in a large number of cases.

Condition f) can basically lead to immediate damage, for example, because a seal is pressed out of its seating, whereupon a lack of sealing leads to escape of medium from the pipeline. Even when condition f) is not fulfilled, multiply repeating pressure spikes can over a long period of time lead to damage, which can evidence itself e.g. by failure of measuring devices.

The previously mentioned conditions in pipes are almost unavoidable, however, they are still not sufficient for the occurrence of condensation induced hydraulic shock. This is due to the remaining condition b). Only, when the temperature difference between vapor ($T_S$) and condensate ($T_K$) is sufficiently large, is then the risk of condensation induced hydraulic shock significant. Now, it is the case that exactly condition b) can be externally influenced, thus by choice of the operating states. Therefore, a monitoring of the temperatures is sufficient for early warning against condensation induced hydraulic shock.

The invention can be embodied in many different forms, which are subject matter of the dependent claims. Especially, different ways of arranging the temperature sensors on or in the pipe are possible.

It is advantageous, when the first temperature sensor and the second temperature sensor are, respectively, subcomponents of a first temperature detector with a first housing and a second temperature detector with a second housing, wherein the first temperature detector and the second temperature detector are mounted to the wall of the pipe and protrude into the interior of the pipe, and wherein the first temperature detector and the second temperature detector are so arranged in the pipe that the first temperature sensor and the second temperature sensor do not contact the wall of the pipe. Each temperature detector comprises thus a temperature sensor and a housing. Moreover, a temperature detector comprises, of course, also possible electronic components for read out and evaluation of the temperature and, in given cases, also an energy supply unit. Preferably, the housing provides insulation from the wall of the pipe. The insulation should be embodied in such a manner that the temperature of the wall has no influence on the temperature measurement of each of the two temperature sensors. For example, the housing can have a cylindrical shape, whose penetration depth into the pipe is correspondingly matched to the respective geometry and whose material has a low thermal conductivity.

In a preferred embodiment, the first temperature detector is mounted in the upper region of the pipe, such that the first temperature sensor is located in the upper third along a vertical, diametral, connecting line through the pipe, and the second temperature detector is mounted in the lower region of the pipe, such that the second temperature sensor is located in the direct vicinity of the wall of the pipe on its lower side. In this way, it can be assured that the the first temperature detector safely measures the temperature of the vapor ($T_V$) and the second temperature detector the temperature of the condensate ($T_K$).

Alternatively, in an additional preferred embodiment, the first temperature detector is mounted in the lower region of the pipe, such that the first sensor element is located in the upper third along a vertical, diametral, connecting line through the pipe, and the second temperature detector is mounted in the upper region of the pipe, such that the second sensor element is located in the direct vicinity of the wall of the pipe on its lower side. In this example, the first temperature detector measures again the temperature of the vapor ($T_V$), while the second temperature detector measures again the temperature of the condensate ($T_K$). This arrangement of the first temperature detector extending from the lower region has the advantage that condensate running on the housing of the second temperature detector does not influence the measuring of the temperature of the vapor ($T_V$). It is important in the case of this embodiment that each of the two temperature detectors is positioned in such a manner that it approaches the respectively oppositely lying wall of the pipe but does not contact such.

In an especially preferred embodiment, the first temperature detector and the second temperature detector are both mounted in the upper region of the pipe or in the lower region of the pipe, wherein the two housings have different lengths. In the case of an arrangement extending from the same side of the housing, the two temperature detectors can especially simply be contacted with one another, in order to determine the temperature difference.

In an alternative embodiment, the first temperature sensor and the second temperature sensor are arranged in one temperature detector with one housing, wherein the temperature detector is mounted to the wall of the pipe and protrudes inwardly into the interior of the pipe, and wherein the temperature detector is so arranged in the pipe that the first temperature sensor and the second temperature sensor do not contact the wall of the pipe. This embodiment is implementable more compactly than those described above.

It is, moreover, advantageous, when the temperature detector is mounted in the upper region of the pipe or in the lower region of the pipe, wherein the housing is essentially rod-shaped, and wherein the two temperature sensors are arranged in different regions of the housing, such that the first temperature sensor is located in the region of the condensed part of the fluid, and the second temperature sensor is located in the region, in which the fluid is present in the vapor phase.

In an especially preferred embodiment, a pressure sensor is integrated into the wall of the pipe and embodied to register the static pressure in the pipe, wherein a vapor pressure curve of the fluid is furnished in the electronics unit, and wherein a report is generated only when, supplementally to exceeding the limit value for the temperature difference, the temperature of the vapor is greater than a reference temperature corresponding to the measured static pressure according to the vapor pressure curve. The additional measuring of the static pressure supplementally increases the predictive accuracy for the occurrence of condensation induced hydraulic shock.

The object of the invention is, furthermore, achieved by a method for early warning against condensation induced hydraulic shock and/or steam hammer in a component, especially a pipe, conveying a fluid, which is present in at least a first part in the vapor phase and, in the case of condensate formation, in a second part in the form of a condensate, wherein the temperature of the vapor is measured, wherein the temperature of the condensate is measured, wherein the temperature difference between the temperature of the vapor and the temperature of the condensate is ascertained, and wherein a report is generated upon reaching a predetermined limit value for the temperature difference.

In such case, it is advantageous to measure the static pressure in the pipe, wherein the temperature of the vapor is compared with the reference temperature belonging to the static pressure according to a vapor pressure curve, and wherein a report is generated only when the temperature of the vapor is greater than the reference temperature.

The apparatus of the invention and/or the method of the invention as claimed in at least one of the claims is used preferably in process and/or automation technology.

BRIEF DESCRIPTION OF THE DRAWINGS

The invention as well as its advantages will now be explained in greater detail based on the appended drawing, the figures of which show as follows.

DETAILED DISCUSSION IN CONJUNCTION WITH THE DRAWINGS

Figure 1:
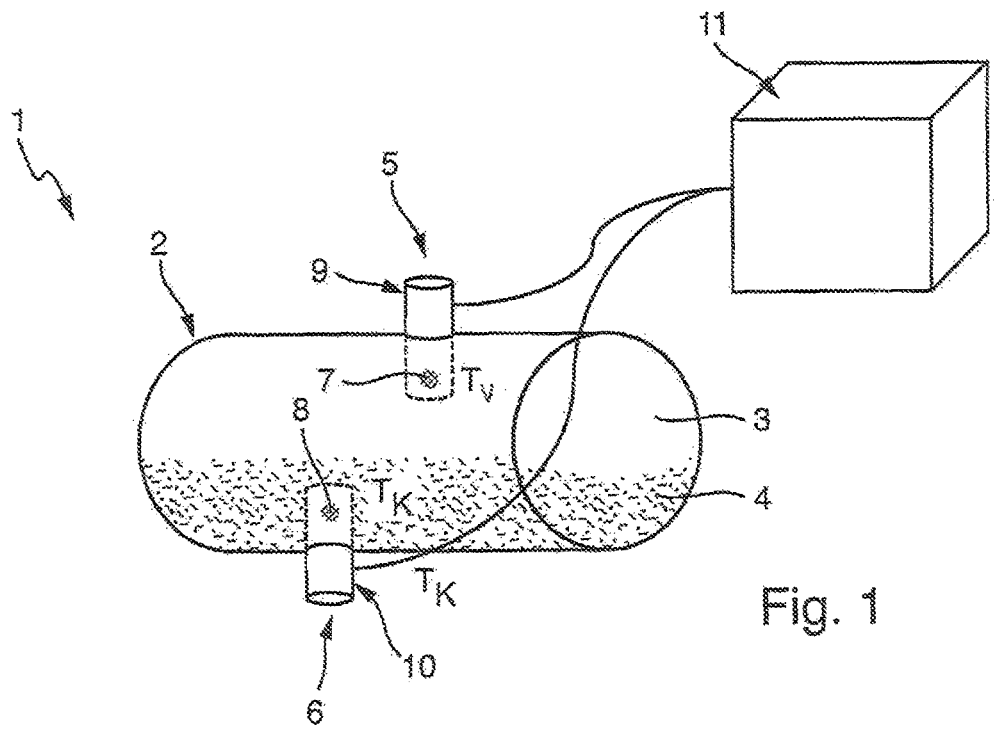
FIG. 1 is a schematic drawing of an embodiment of the apparatus of the invention.

In the figures, equal features are provided with equal reference characters. The apparatus of the invention in its totality bears the reference character 1. One or more primes on a reference character refer to respectively different examples of embodiments.

FIG. 1 shows a schematic drawing of a first example of an embodiment of an apparatus 1 of the invention as defined in claim 3. Shown is a pipe 2, through which is flowing a fluid present in a first part in the vapor phase, thus vapor 3, and in a second part as condensate 4. Mounted on the wall of the pipe 2 are two temperature detectors 5, 6 having respective temperature sensors 7, 8 and respective housings 9, 10. Temperature detectors 5, 6 protrude into the interior of the pipe 2. Temperature detectors 5, 6 are not in contact with the wall of the pipe 2, so that the temperature of the wall does not influence the measurements of the respective temperatures ($T_V$), ($T_K$) of the vapor 3 and condensate 4. In this example, the first temperature detector 5 measures the temperature ($T_V$) of the vapor 3 and the second temperature detector 6 the temperature ($T_K$) of the condensate 4. Within the electronics unit 11, finally, at determinable points in time, in each case, the temperature difference $\Delta T = T_V - T_K$ is ascertained and, upon the exceeding of a certain determinable limit value, a report is generated.

Figure 2:
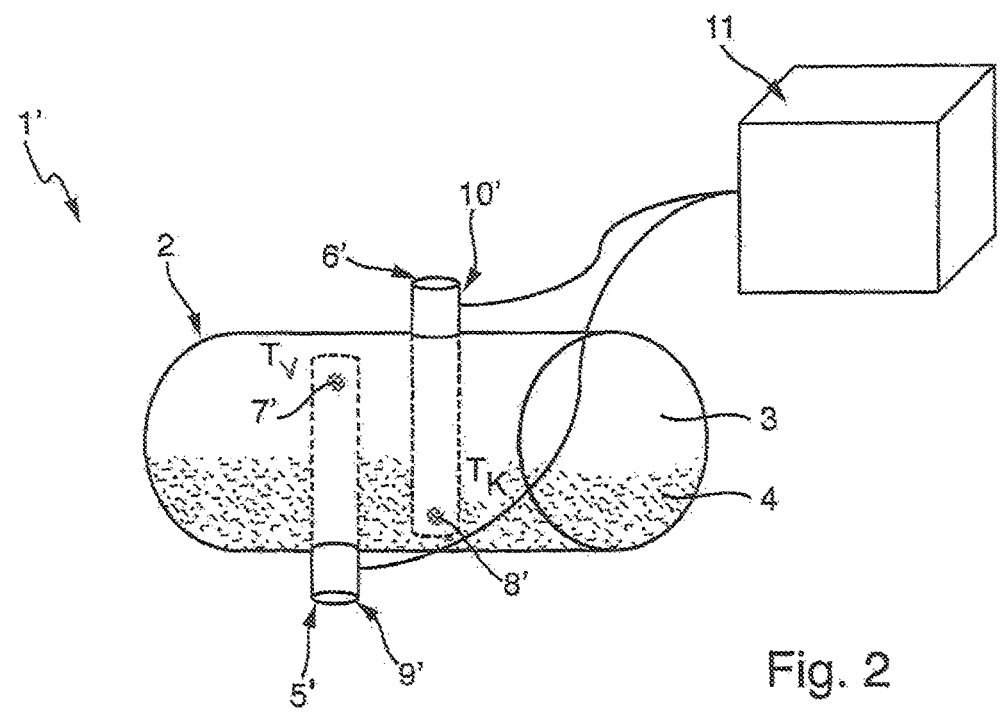
FIG. 2 is a schematic drawing of a further embodiment of the apparatus of the invention.

A further example of an embodiment for an apparatus 1' of the invention is shown in FIG. 2. Again, the pipe 2 is present, through which is flowing a fluid present in a first part as a vapor 3, and in a second part as a condensate 4. The first temperature detector 5' is mounted in the lower region of the pipe 2, such that the first temperature sensor 7' is arranged in the upper third along a vertical, diametral, connecting line (not shown) through the pipe 2. The second temperature detector 6', in contrast, is mounted in the upper region of the pipe 2, such that the second temperature sensor 8' is located in the direct vicinity of the wall of the pipe 2 on its lower side. In this case, again, the first temperature detector 5' measures the temperature ($T_V$) of the vapor 3 and the second temperature detector 6' the temperature ($T_K$) of the condensate 4. The installation of the second temperature detector 5' in the lower region of the pipe 2 has the advantage that condensate depositing on this temperature detector 5' does not influence the measuring of the temperature ($T_V$) of the vapor 3.

The two temperature detectors are positioned in such a manner that they approach the oppositely lying wall of the pipe 2 but do not contact it.

Figure 3:
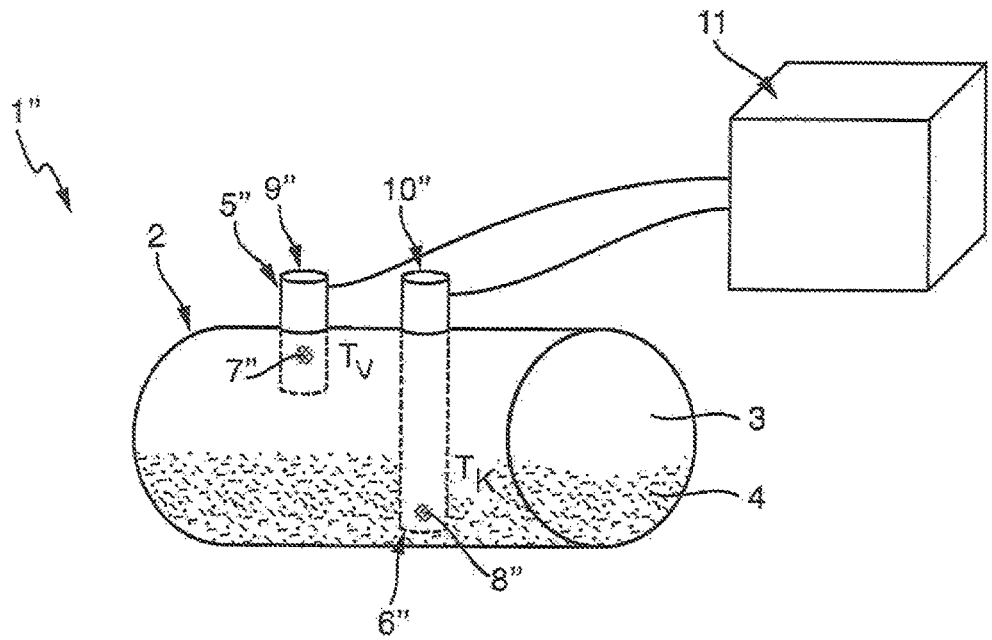
FIG. 3 is a schematic drawing a further embodiment of the apparatus of the invention.

FIG. 3 shows an embodiment of an apparatus 1" of the invention according to claim 5. The first 5" and second 6" temperature detectors are both mounted in the upper region of the pipe 2. This assures that one of the two temperature detectors 5", 6" registers the temperature of the vapor 3 and the other that of the condensate 4. The two housings 9", 10" of the two temperature detectors 5", 6" have different lengths, and each of the temperature sensors 7", 8" is arranged in the end region of the respective housing 9", 10". Of course, the two temperature detectors 5", 6" can also be mounted in the lower region of the pipe 2 to its wall.

Figure 4:
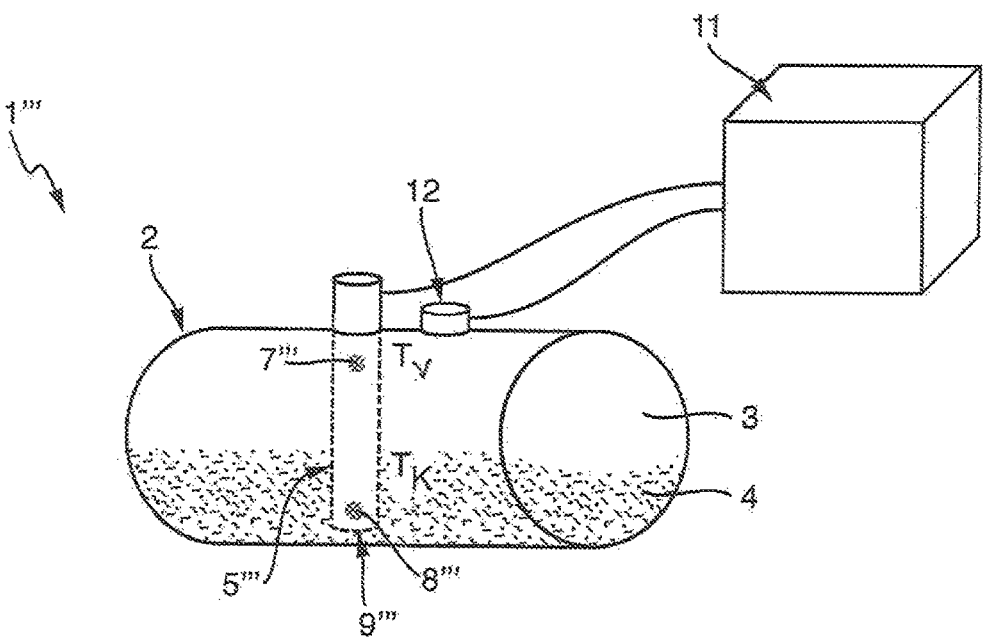
FIG. 4 is a schematic drawing of a further embodiment of the apparatus of the invention, and with an additional pressure sensor.

Another alternative for an apparatus 1''' of the invention is shown in FIG. 4. The two temperature sensors 7''', 8''' are arranged in one temperature detector 5' having a housing 9'''. Temperature detector 5''' is mounted to the wall of the pipe 2 and protrudes into its interior. While the temperature detector 5''' in this view is mounted in the upper region of the pipe, it can, of course, in another variant also be secured in the lower region of the pipe 2. Housing 9''' is essentially rod-shaped and the two temperature sensors 7''', 8''' are arranged in different regions of the housing 9'''. In each case, it must be assured that one of the two temperature sensors 7''', in the view shown here the first, reliably measures the temperature of the vapor 3 and the other of the two temperature sensors 8''', in the view shown here the second, reliably measures the temperature ($T_K$) of the condensate 4.

FIG. 4 also shows a pressure sensor 12 of claim 8. This is optional and, thus, does not have to be present in an embodiment according to FIG. 4. Pressure sensor 12 serves to register the static pressure in the pipeline. This, in turn, in given cases, increases the reliability of prediction of possible condensation induced, hydraulic shock within the pipeline.

The following are possible operating states of an apparatus 1, 1', 1", 1''' of the invention and explain possible scenarios of the method of the invention:

a) The pipe 2 is flowed through exclusively by vapor 3 and is free of condensate 4. In this case, the two temperature sensors 7, 8 show, to within a few degrees, the same temperature. Correspondingly, the ascertained temperature difference $\Delta T = T_V - T_K$ is small and no report is generated.

b) The pipe 2 is completely filled with condensate 4 and carries no vapor 3. Also in this case, the temperature difference $\Delta T = T_V - T_K$ amounts, at most, to a few degree Kelvin and no report is generated.

c) When the pipe 2 is flowed through partially by vapor 3 and partially by condensate 4, the temperature difference $\Delta T = T_V - T_K$ amounts in the normal case likewise to only a few degrees Kelvin. Also, in such case, no report is generated.

d) If the pipe 2 is flowed through in the case c) partially by condensate 4 and partially by vapor 3, and the temperature difference $\Delta T = T_V - T_K$ between both phases exceeds a determinable limit value, for example, 20K, a report is generated. In the case, in which, supplementally, a pressure sensor 11 is present, the report is only generated when the measured temperature ($T_V$) of the vapor 4 equals or is greater than the reference temperature ($T_R$) belonging to the measured static pressure and determined based on a vapor pressure curve.

Of course, numerous other arrangements of the two temperature detectors 5, 6 may be applied, which likewise fall within the scope of the invention. Likewise, more than two temperature sensors 7, 8 can be used. Furthermore, the most varied of options for contacting the temperature sensors 7, 8 with one another and for connecting with, as well as the arrangement of, an electronics unit 11 can be provided. The exact implementing of an evaluation of the temperature measurement depends on these features. The same is true for the temperature detectors 5, 6, the arrangement of at least one temperature sensor 7, 8 in a temperature detector 5, 6 and the embodiment of the respective housings 9, 10. Finally, also various options for securing the temperature sensors 7, 8 in the temperature detector 5, 6, respectively for securing the temperature detectors 5,6 to the wall of the pipe 2, as well as their sealed integration right into the pipe interior, are available, and have not been described in detail here.

The invention claimed is:

1. An apparatus for early warning against condensation induced hydraulic shock in a pipe conveying a fluid present at least in a first part in the vapor phase and, in the case of condensate formation, in a second part in the form of a condensate, comprising:
   at least two temperature sensors, which are arranged in the pipe and, thus, are fluid contacting; and
   at least one electronics unit, wherein:
   a first temperature sensor of said at least two temperature sensors is so arranged that it measures the temperature of the vapor:
   wherein a second temperature sensor of said at least two temperature sensors is so arranged that it measures the temperature of the condensate; and
   said at least one electronics unit is so embodied that it ascertains the temperature difference ($\Delta T$) between the temperature of the vapor and the temperature of the condensate, and, upon reaching a predetermined limit value for the temperature difference ($\Delta T$), generates a report for early warning against condensation induced hydraulic shock.

2. The apparatus as claimed in claim 1, wherein:
   said first temperature sensor and said second temperature sensor are subcomponents of a first temperature detector with a first housing;
   a second temperature detector with a second housing;
   said first temperature detector and said second temperature detector are mounted to the wall of said pipe and protrude into the interior of said pipe; and
   said first temperature detector and said second temperature detector are so arranged in the pipe that said first temperature sensor and said second temperature sensor do not contact the wall of said pipe.

3. The apparatus as claimed in claim 2, wherein:
   said first temperature detector and said second temperature detector are both mounted in the upper region of said pipe or in the lower region of said pipe; and
   said first housing and said second housing have different lengths.

4. The apparatus as claimed in claim 1, wherein:
   said first temperature detector is mounted in the upper region of said pipe, such that said first temperature sensor is located in the upper third along a vertical, diametral, connecting line through said pipe; and
   said second temperature detector is mounted in the lower region of said pipe, such that said second temperature sensor is located in the direct vicinity of the wall of said pipe on its lower side.

5. The apparatus as claimed in claim 1, wherein:
   said first temperature detector is mounted in the lower region of said pipe, such that said first sensor element is located in the upper third along a vertical, diametral, connecting line through said pipe; and
   said second temperature detector is mounted in the upper region of said pipe, such that said second sensor element is located in the direct vicinity of the wall of said pipe on its lower side.

6. The apparatus as claimed in claim 1, wherein:
   said first temperature sensor and said second temperature sensor are arranged in one temperature detector with one housing;
   said temperature detector is mounted to the wall of said pipe and protrudes inwardly into the interior of said pipe; and
   said temperature detector is so arranged in said pipe that said first temperature sensor and said second temperature sensor do not contact the wall of said pipe.

7. The apparatus as claimed in claim 6, wherein:
   said temperature detector is mounted in the upper region of said pipe or in the lower region of said pipe;
   said housing is essentially rod-shaped; and
   said two temperature sensors are arranged in different regions of said housing, such that said first temperature sensor is located in the region of said condensed part of the fluid, and said second temperature sensor is located in the region, in which the fluid is present in the vapor phase.

8. The apparatus as claimed in claim 1, further comprising:
   a pressure sensor integrated into the wall of said pipe and embodied to register the static pressure in said pipe;
   a vapor pressure curve of the fluid is furnished in said electronics unit, and a report is generated only when, additionally to exceeding the limit value for the temperature difference, the temperature of the vapor is greater than a reference temperature corresponding to the measured static pressure according to the vapor pressure curve.

9. A method for early warning against condensation induced hydraulic shock and/or steam hammers in a pipe conveying a fluid, which is present in at least a first part in the vapor phase and, in the case of condensate formation, in a second part in the form of a condensate, comprising the steps of:
   measuring the temperature of the vapor;
   measuring the temperature of the condensate; and
   ascertaining the temperature difference ($\Delta T$) between the temperature of the vapor and the temperature of the condensate, wherein:
   a report is generated upon reaching a predetermined limit value for the temperature difference ($\Delta T$) for early warning against condensation induced hydraulic shock.

10. The method as claimed in claim 9, further comprising the steps of:
   measuring the static pressure in said pipe;
   comparing the temperature of the vapor with the reference temperature belonging to the static pressure according to a vapor pressure curve; and generating a report only when the temperature of the vapor is greater than the reference temperature.

\* \* \* \* \*